US008622059B2

(12) United States Patent
Kleman

(10) Patent No.: US 8,622,059 B2
(45) Date of Patent: Jan. 7, 2014

(54) FACE MASK WITH ABSORBENT ELEMENT

(75) Inventor: Angela M. Kleman, Toledo, OH (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 956 days.

(21) Appl. No.: 11/022,379

(22) Filed: Dec. 21, 2004

(65) Prior Publication Data

US 2006/0130842 A1 Jun. 22, 2006

(51) Int. Cl.

| | |
|---|---|
| ***A62B 23/02*** | (2006.01) |
| ***A62B 9/04*** | (2006.01) |
| ***A62B 7/10*** | (2006.01) |
| ***A61M 16/06*** | (2006.01) |

(52) U.S. Cl.
USPC ............ 128/206.19; 128/206.12; 128/205.29; 128/203.12; 128/203.29; 128/200.24

(58) Field of Classification Search
USPC ............. 128/206.19, 206.12, 206.14, 206.17, 128/206.24, 206.25, 205.27, 205.29, 128/206.21, 206.22, 206.13, 857, 863, 859, 128/201.17, 201.22, 201.23, 201.25, 128/202.27, 203.29, 204.11, 204.12, 128/204.13, 205.25, 206.16, 205.28, 206.18
See application file for complete search history.

(56) References Cited

U.S. PATENT DOCUMENTS

| | | | | | |
|---|---|---|---|---|---|
| 2,435,721 | A | * | 2/1948 | Lehmann | 128/206.17 |
| 3,170,461 | A | * | 2/1965 | Watts, Jr. | 128/863 |
| 3,338,992 | A | | 8/1967 | Kinney | |
| 3,341,394 | A | | 9/1967 | Kinney | |
| 3,502,763 | A | | 3/1970 | Hartmann | |
| 3,542,615 | A | | 11/1970 | Dobo et al. | |
| 3,603,315 | A | * | 9/1971 | Becker, III | 128/206.19 |
| 3,692,618 | A | | 9/1972 | Dorschner et al. | |
| 3,802,817 | A | | 4/1974 | Matsuki et al. | |
| 3,849,241 | A | | 11/1974 | Butin et al. | |
| 3,953,566 | A | | 4/1976 | Gore | |
| 4,095,290 | A | * | 6/1978 | O'Brien | 2/9 |
| 4,100,324 | A | | 7/1978 | Anderson et al. | |
| 4,187,390 | A | | 2/1980 | Gore | |
| 4,215,682 | A | | 8/1980 | Kubik et al. | |
| 4,259,748 | A | | 4/1981 | Miller | |
| 4,340,563 | A | | 7/1982 | Appel et al. | |
| 4,374,888 | A | | 2/1983 | Bornslaeger | |
| 4,375,718 | A | | 3/1983 | Wadsworth et al. | |
| 4,419,994 | A | * | 12/1983 | Hilton | 128/206.19 |
| 4,443,513 | A | | 4/1984 | Meitner et al. | |
| 4,592,815 | A | | 6/1986 | Nakao | |
| 4,631,933 | A | | 12/1986 | Carey, Jr. | |
| 4,652,487 | A | | 3/1987 | Morman | |
| 4,655,760 | A | | 4/1987 | Morman et al. | |

(Continued)

OTHER PUBLICATIONS

U.S. Appl. No. 10/970,457, filed Oct. 21, 2004.

(Continued)

*Primary Examiner* — Annette Dixon
(74) *Attorney, Agent, or Firm* — Dority & Manning, P.A.

(57) ABSTRACT

A face mask for reducing or eliminating fogging of eye wear worn by a user of the face mask is provided. The face mask may include a body portion that has an outer surface and an oppositely disposed inner surface. The face mask may also have an absorbent element that may be located on at least one of the surfaces of the body portion. The absorbent element may be capable of absorbing at least 3.5 grams of water and may act to absorb moisture and/or condensation due to human respiration and/or perspiration.

9 Claims, 4 Drawing Sheets

(56) References Cited

U.S. PATENT DOCUMENTS

| | | | | | |
|---|---|---|---|---|---|
| 4,657,802 | A | | 4/1987 | Morman | |
| 4,662,005 | A | * | 5/1987 | Grier-Idris | 2/9 |
| 4,720,415 | A | | 1/1988 | Vander Wielen et al. | |
| 4,781,966 | A | | 11/1988 | Taylor | |
| 4,789,699 | A | | 12/1988 | Kieffer et al. | |
| 4,802,473 | A | | 2/1989 | Hubbard et al. | |
| 4,818,464 | A | | 4/1989 | Lau | |
| 4,874,659 | A | | 10/1989 | Ando et al. | |
| 4,891,957 | A | | 1/1990 | Strack et al. | |
| 4,920,960 | A | * | 5/1990 | Hubbard et al. | 128/206.12 |
| 4,941,467 | A | * | 7/1990 | Takata | 128/203.12 |
| 4,965,122 | A | | 10/1990 | Morman | |
| 4,969,457 | A | * | 11/1990 | Hubbard et al. | 128/206.12 |
| 4,981,747 | A | | 1/1991 | Morman | |
| 5,020,533 | A | | 6/1991 | Hubbard et al. | |
| 5,033,128 | A | * | 7/1991 | Torres | 2/427 |
| 5,094,236 | A | * | 3/1992 | Tayebi | 128/206.12 |
| 5,114,781 | A | | 5/1992 | Morman | |
| 5,226,992 | A | | 7/1993 | Morman | |
| 5,244,482 | A | | 9/1993 | Hassenboehler, Jr. et al. | |
| 5,322,061 | A | | 6/1994 | Brunson | |
| 5,336,545 | A | | 8/1994 | Morman | |
| 5,372,130 | A | * | 12/1994 | Stern et al. | 128/205.25 |
| 5,383,450 | A | | 1/1995 | Hubbard et al. | |
| 5,401,466 | A | | 3/1995 | Foltz et al. | |
| 5,467,765 | A | * | 11/1995 | Maturaporn | 128/206.19 |
| 5,492,753 | A | | 2/1996 | Levy et al. | |
| 5,493,753 | A | | 2/1996 | Rostamo | |
| 5,540,976 | A | | 7/1996 | Shawver et al. | |
| 5,553,608 | A | | 9/1996 | Reese et al. | |
| 5,681,645 | A | | 10/1997 | Strack et al. | |
| 5,699,791 | A | | 12/1997 | Sukiennik et al. | |
| 5,706,804 | A | * | 1/1998 | Baumann et al. | 128/206.19 |
| 5,727,544 | A | * | 3/1998 | Miura | 128/201.13 |
| 5,803,077 | A | * | 9/1998 | Gazzara | 128/205.27 |
| 5,813,398 | A | | 9/1998 | Baird et al. | |
| 5,934,275 | A | * | 8/1999 | Gazzara | 128/205.27 |
| 5,976,117 | A | * | 11/1999 | Dunshee et al. | 604/307 |
| 6,062,220 | A | | 5/2000 | Whitaker et al. | |
| 6,079,980 | A | * | 6/2000 | Durand | 433/137 |
| 6,362,389 | B1 | * | 3/2002 | McDowall et al. | 604/367 |
| 6,375,724 | B1 | * | 4/2002 | Foti | 96/294 |
| 6,412,486 | B1 | | 7/2002 | Glass | |
| 6,474,336 | B1 | | 11/2002 | Wolfe | |
| 6,484,722 | B2 | | 11/2002 | Bostock et al. | |
| 6,520,181 | B2 | | 2/2003 | Baumann et al. | |
| 6,568,392 | B1 | * | 5/2003 | Bostock et al. | 128/206.19 |
| 6,644,314 | B1 | | 11/2003 | Elsberg | |
| 7,017,577 | B2 | * | 3/2006 | Matich | 128/206.14 |
| 7,619,130 | B2 | * | 11/2009 | Nielsen et al. | 602/58 |
| 2004/0078869 | A1 | | 4/2004 | Bell et al. | |
| 2004/0121107 | A1 | | 6/2004 | Bell et al. | |
| 2005/0133035 | A1 | * | 6/2005 | Yahiaoui et al. | 128/206.19 |
| 2005/0194010 | A1 | * | 9/2005 | Sankot | 128/206.19 |
| 2006/0005838 | A1 | * | 1/2006 | Magidson | 128/206.19 |

OTHER PUBLICATIONS

U.S. Appl. No. 10/743,260, filed Dec. 22, 2003.
U.S. Appl. No. 11/020,738, filed Dec. 22, 2004.
U.S. Appl. No. 11/020,734, filed Dec. 22, 2004.
U.S. Appl. No. 11/021,543, filed Dec. 23, 2004.

* cited by examiner

FACE MASK WITH ABSORBENT ELEMENT

BACKGROUND

Face masks find utility in a variety of medical, industrial and household applications by protecting the wearer from inhaling dust and other harmful airborne contaminates through their mouth or nose. The use of face masks is a recommended practice in the healthcare industry to help prevent the spread of disease. Face masks worn by healthcare providers help reduce infections in patients by filtering the air exhaled from the wearer thus reducing the number of harmful organisms or other contaminants released into the environment. Additionally, face masks protect the healthcare worker by filtering airborne contaminants and microorganisms from the inhaled air.

The section of the face mask that covers the nose and mouth is typically known as the body portion. The body portion of the mask may be comprised of several layers of material. At least one layer may be composed of a filtration material that prevents the passage of germs and other contaminants therethrough but allows for the passage of air so that the user may comfortably breathe. The porosity of the mask refers to how easily air is drawn through the mask. A more porous mask is easier to breathe through. The body portion may also contain multiple layers to provide additional functionality or attributes to the face mask. For example, many face masks include one or more layers of material on either side of the filtration media layer. Further components may be attached to the mask to provide additional functionality. A clear plastic face shield intended to protect the user's face from splashed fluid is one example.

When using a properly donned face mask, the heat and moisture of the user's exhaled breath tends to concentrate inside. As this humidified air escapes the face mask, it can condense on the user's eye wear or face shield causing fogging which may hamper the sight of the healthcare worker.

A method to eliminate fogging of eye wear or face shields resides in providing a seal across the upper edge of the face mask and the user's face to prevent moisture from escaping upwards. Aside from being uncomfortable, the seal on the face of the user is not always complete and moisture may be able to escape therethrough. Additionally, moisture may escape through the body portion of the face mask and subsequently condense on the eye wear or face shield.

Another attempt to reduce fogging has been made by providing an absorbent core between an inner and outer layer of the face mask. This approach may be problematic, for example, in that moisture may propagate along the inner surface of the inner layer of the face mask and exit therefrom so as to condense on the eye wear or face shield without contacting the absorbent core.

SUMMARY

Various features and advantages of the invention will be set forth in part in the following description, or may be obvious from the description, or may be learned from practice of the invention.

A face mask is provided in one exemplary embodiment that includes a body portion with an outer surface and an inner surface oppositely disposed to the outer surface. The face mask may also include an absorbent element located on at least one of the surfaces of the body portion. The absorbent element may be capable of absorbing at least 3.5 grams of water. The face mask is advantageous in that moisture and/or condensation produced through human respiration and/or perspiration may be absorbed by the absorbent element when the face mask is worn so as to reduce or eliminate fogging that may occur on eye wear worn by the user and/or to reduce condensation build-up on the face of the user.

Another exemplary embodiment of the face mask includes a body portion configured to be placed over the mouth and at least part of the nose of the user. The body portion isolates the mouth and the at least part of the nose of the user from the environment so that respiration air is drawn through the body portion and subsequently exhaled by the user through the body portion. The body portion has an outer surface that faces away from the user when worn and an inner facing surface that faces towards the user when worn. A fastening member may be included and may be attached to a body portion and configured for retaining the body portion onto the face of a user. An absorbent element may also be included and located on at least one of the surfaces of the body portion. The absorbent element is configured for retaining liquid and may be capable of absorbing at least 3.5 grams of water.

An exemplary embodiment as previously discussed also exists in which the absorbent element is capable of absorbing between 3.7 and 5.9 grams of water.

In an exemplary embodiment as discussed above, the absorbent element may be located on the inner surface of the body portion. Alternatively, the absorbent element may be located on the outer surface of the body portion. Further, the absorbent element may be located on both the outer surface and inner surface of the body portion in another exemplary embodiment.

Another exemplary embodiment exists in which the face mask as previously discussed may have an absorbent element that is rectangular shaped. The absorbent element may be positioned so as to extend across at least a portion of the horizontal length of the body portion.

Also, a face mask as previously discussed may be provided where the absorbent element is located on one of the surfaces of the body portion so as to form a perimeter that bounds an area of the surface. Also provided for is an exemplary embodiment as discussed above where the absorbent element is located around the perimeter of the surface.

With an embodiment of a face mask as previously discussed, the absorbent element may be treated with a surfactant in order to increase the hydrophilic property of the absorbent element so that the absorbent element is more liquid absorbent.

Also provided is an exemplary embodiment of the face mask where the absorbent element may be made at least partially of cellulosic fibers.

These and other features, aspects and advantages of the present invention will become better understood with reference to the following description and appended claims. The accompanying drawings, which are incorporated in and constitute part of this specification, illustrate embodiments of the invention and, together with the description, serve to explain principles of the invention.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

The absorbent element is located on both the outer and inner surfaces of the body portion.

Figure 6:
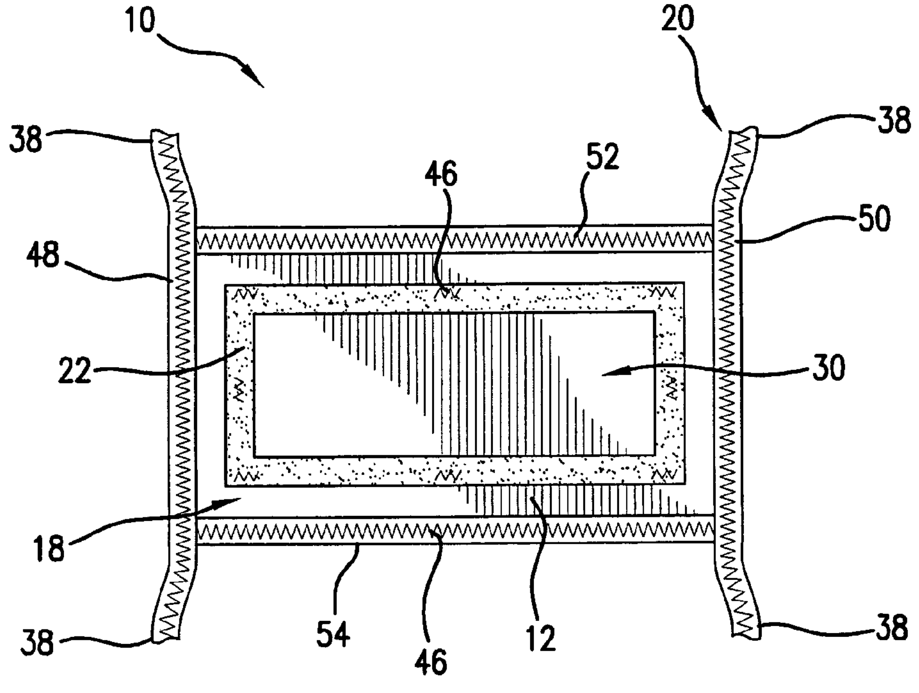

FIG. 6 is a back view of an exemplary embodiment of a face mask. The absorbent element is located on the inner surface of the body portion and forms a perimeter bounding an area of the inner surface.

Figure 7:
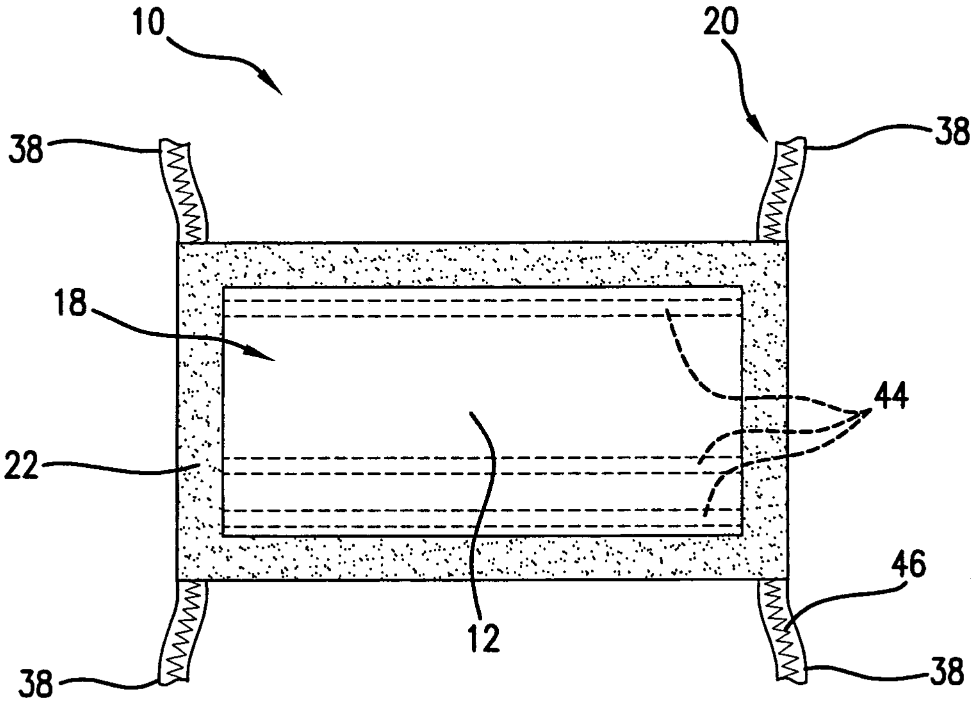

FIG. 7 is a back view of an exemplary embodiment of a face mask. The absorbent element is located around the perimeter of the inner surface of the body portion.

Repeat use of reference characters in the present specification and drawings is intended to present same or analogous features or elements of the invention.

Definitions

As used herein, the term "nonwoven fabric or web" means a web having a structure of individual fibers or threads which are interlaid, but not in an identifiable manner as in a knitted fabric. Nonwoven fabrics or webs have been formed from various processes such as, for example, meltblowing processes, spunbonding processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

As used herein, the term "ultrasonic bonding" refers to a process in which materials (fibers, webs, films, etc.) are joined by passing the materials between a sonic horn and anvil roll. An example of such a process is illustrated in U.S. Pat. No. 4,374,888 to Bornslaeger, the entire contents of which are incorporated herein by reference in their entirety for all purposes.

As used herein, the term "thermal point bonding" involves passing materials (fibers, webs, films, etc.) to be bonded between a heated calender roll and a heated anvil roll. The calender roll is usually, though not always, engraved with a pattern in some way such that the entire fabric is not bonded across its entire surface. The surface of the anvil roll is usually flat and/or smooth. As a result, various patterns for calender rolls have been developed for functional as well as aesthetic reasons. Typically, the percent bonding area varies from around 10 percent to around 30 percent of the area of the fabric laminate. The bonded areas are typically discrete points or shapes and not interconnected. As is well known in the art, thermal point bonding holds the laminate layers together and imparts integrity and strength to the nonwoven material by bonding filaments and/or fibers together thereby limiting their movement.

As used herein, the term "thermal pattern bonding" involves passing materials (fibers, webs, films, etc.) to be bonded between a heated calender roll and an anvil roll as with thermal point bonding. The difference is that the bonded areas are interconnected producing discrete areas of unbonded fibers. Various patterns for calender rolls have been developed for functional as well as aesthetic reasons. Typically, the percent bonding area varies from around 10 percent to around 30 percent of the area of the fabric laminate.

As used herein, the term "electret" or "electret treating" refers to a treatment that imparts a charge to a dielectric material, such as a polyolefin. The charge includes layers of positive or negative charges trapped at or near the surface of the polymer, or charge clouds stored in the bulk of the polymer. The charge also includes polarization charges which are frozen in alignment of the dipoles of the molecules. Methods of subjecting a material to electret treating are well known by those skilled in the art. These methods include, for example, thermal, liquid-contact, electron beam, and corona discharge methods. One particular technique of subjecting a material to electret treating is disclosed in U.S. Pat. No. 5,401,466 to Foltz, the entire contents of which are herein incorporated by reference in their entirety for all purposes. This technique involves subjecting a material to a pair of electrical fields wherein the electrical fields have opposite polarities.

As used herein, the term "spunbonded fibers" refers to small diameter fibers which are formed by extruding molten thermoplastic material as filaments from a plurality of fine, usually circular capillaries of a spinneret with the diameter of the extruded filaments then being rapidly reduced to fibers as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al., the entire contents of which are incorporated herein by reference in their entirety for all purposes. Spunbond fibers are generally continuous and have diameters generally greater than about 7 microns, more particularly, between about 10 and about 40 microns.

As used herein, the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al., the entire contents of which are incorporated herein by reference in their entirety for all purposes. Meltblown fibers are microfibers which may be continuous or discontinuous with diameters generally less than 10 microns.

As used herein, the term "stretch bonded laminate" refers to a composite material having at least two layers in which one layer is a gatherable layer and the other layer is an elastic layer. The layers are joined together when the elastic layer is extended from its original condition so that upon relaxing the layers, the gatherable layer is gathered. Such a multilayer composite elastic material may be stretched to the extent that the nonelastic material gathered between the bond locations allows the elastic material to elongate. One type of stretch bonded laminate is disclosed, for example, by U.S. Pat. No. 4,720,415 to Vander Wielen et al., the entire contents of which are incorporated herein by reference in their entirety for all purposes. Other composite elastic materials are disclosed in U.S. Pat. No. 4,789,699 to Kieffer et al., U.S. Pat. No. 4,781,966 to Taylor and U.S. Pat. No. 4,657,802 and U.S. Pat. No. 4,652,487 to Morman and U.S. Pat. No. 4,655,760 to Morman et al., the entire contents of which are incorporated herein by reference in their entirety for all purposes.

As used herein, the terms "necking" or "neck stretching" interchangeably refer to a method of elongating a nonwoven fabric, generally in the machine direction, to reduce its width (cross-machine direction) in a controlled manner to a desired amount. The controlled stretching may take place under cool, room temperature or greater temperatures and is limited to an increase in overall dimension in the direction being stretched up to the elongation required to break the fabric, which in most cases is about 1.2 to 1.6 times. When relaxed, the web retracts toward, but does not return to, its original dimensions. Such a process is disclosed, for example, in U.S. Pat. No. 4,443,513 to Meitner and Notheis, U.S. Pat. Nos. 4,965,122, 4,981,747 and 5,114,781 to Morman and U.S. Pat. No. 5,244, 482 to Hassenboehler Jr. et al., the entire contents of which are incorporated herein by reference in their entirety for all purposes.

As used herein, the term "necked material" refers to any material which has undergone a necking or neck stretching process.

As used herein, the term "reversibly necked material" refers to a material that possesses stretch and recovery characteristics formed by necking a material, then heating the necked material, and cooling the material. Such a process is disclosed in U.S. Pat. No. 4,965,122 to Morman, the entire contents of which are incorporated herein by reference in their entirety for all purposes.

As used herein, the term "neck bonded laminate" refers to a composite material having at least two layers in which one layer is a necked, non-elastic layer and the other layer is an elastic layer. The layers are joined together when the non-elastic layer is in an extended (necked) condition. Examples of neck-bonded laminates are such as those described in U.S. Pat. Nos. 5,226,992, 4,981,747, 4,965,122 and 5,336,545 to Morman, the entire contents of which are incorporated herein by reference in their entirety for all purposes.

As used herein, the term "coform" means a meltblown material to which at least one other material is added during the meltblown material formation. The meltblown material may be made of various polymers, including elastomeric polymers. Various additional materials may be added to the meltblown fibers during formation, including, for example, pulp, superabsorbent particles, cellulose or staple fibers. Coform processes are illustrated in commonly assigned U.S. Pat. No. 4,818,464 to Lau and U.S. Pat. No. 4,100,324 to Anderson et al., the entire contents of which are incorporated herein by reference in their entirety for all purposes.

As used herein, the term "stitchbonded" refers to a process in which materials (fibers, webs, films, etc.) are joined by stitches sewn or knitted through the materials. Examples of such processes are illustrated in U.S. Pat. No. 4,891,957 to Strack et al. and U.S. Pat. No. 4,631,933 to Carey, Jr., the entire contents of which are incorporated herein by reference in their entirety for all purposes.

As used herein, the term "elastic" refers to any material, including a film, fiber, nonwoven web, or combination thereof, which upon application of a biasing force, is stretchable to a stretched, biased length which is at least about 150 percent, or one and a half times, its relaxed, unstretched length, and which will recover at least 15 percent of its elongation upon release of the stretching, biasing force.

As used herein, the term "extensible and retractable" refers to the ability of a material to extend upon stretch and retract upon release. Extensible and retractable materials are those which, upon application of a biasing force, are stretchable to a stretched, biased length and which will recover a portion, preferably at least about 15 percent, of their elongation upon release of the stretching, biasing force.

As used herein, the terms "elastomer" or "elastomeric" refer to polymeric materials that have properties of stretchability and recovery.

As used herein, the term "stretch" refers to the ability of a material to extend upon application of a biasing force. Percent stretch is the difference between the initial dimension of a material and that same dimension after the material has been stretched or extended following the application of a biasing force. Percent stretch may be expressed as [(stretched length B initial sample length)/initial sample length]×100. For example, if a material having an initial length of one (1) inch is stretched 0.50 inch, that is, to an extended length of 1.50 inches, the material can be said to have a stretch of 50 percent.

As used herein, the term "recover" or "recovery" refers to a contraction of a stretched material upon termination of a biasing force following stretching of the material by application of the biasing force. For example, if a material having a relaxed, unbiased length of one (1) inch is elongated 50 percent by stretching to a length of one and one half (1.5) inches the material would have a stretched length that is 150 percent of its relaxed length. If this exemplary stretched material contracted, that is recovered to a length of one and one tenth (1.1) inches after release of the biasing and stretching force, the material would have recovered 80 percent (0.4 inch) of its elongation.

As used herein, the term "composite" refers to a material which may be a multicomponent material or a multilayer material. These materials may include, for example, spunbond-meltblown-spunbond, stretch bonded laminates, neck bonded laminates, or any combination thereof.

As used herein, the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

These terms may be defined with additional language in the remaining portions of the specification.

Detailed Description Of Representative Embodiments

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges and limits mentioned herein include all ranges located within, and also all values located under or above the prescribed limits. Also, all ranges mentioned herein include all subranges included in the mentioned ranges. For instance, a range from 100-200 also includes ranges from 110-150, 170-190, and 153-162. Further, all limits mentioned herein include all other limits included in the mentioned limit. For example, a limit of up to about 7 also includes a limit of up to about 5, up to about 3, and up to about 4.5.

One exemplary embodiment provides for a face mask 10 that has a body portion 12 with an outer surface 16 and an oppositely disposed inner surface 18. An absorbent element 22 is located on at least one of the surfaces 16 or 18. The absorbent element 22 is capable of absorbing at least 3.5 grams of water so as to capture moisture vapor and/or condensation due to human respiration and perspiration so as to reduce or eliminate fogging of eye wear such as eye wear and or a face shield that may be worn.

The absorbent element 22 may be capable of absorbing between 3.7 and 5.9 grams of water in accordance with various exemplary embodiments. Any amount or range greater than or equal to 3.5 grams of water may be employed in accordance with other exemplary embodiments. For example, the absorbent element 22 may be capable of absorbing greater than 5 grams of water, greater than 7 grams of water, greater than 10 grams of water, greater than 15 grams of water, greater than 20 gram of water, greater than 25 gra ms of water, between 5 and 15 grams of water, between 3.5 and 50.5 grams of water, between 3.7 and 4.3 grams of water, or 8 grams of water in accordance with various exemplary embodiments.

The absorbent element 22 may be capable of absorbing between 3.5 and 6.0 grams of water per gram of fiber of the absorbent element 22 in certain exemplary embodiments. In certain exemplary embodiments, the water capacity of the absorbent member 22 may be between 350-600%. Further, the absorbent element 22 may be capable of absorbing between 3.7 and 4.3 grams of water in an amount of time between 1.25 and 1.6 seconds in certain exemplary embodiments.

Figure 1:
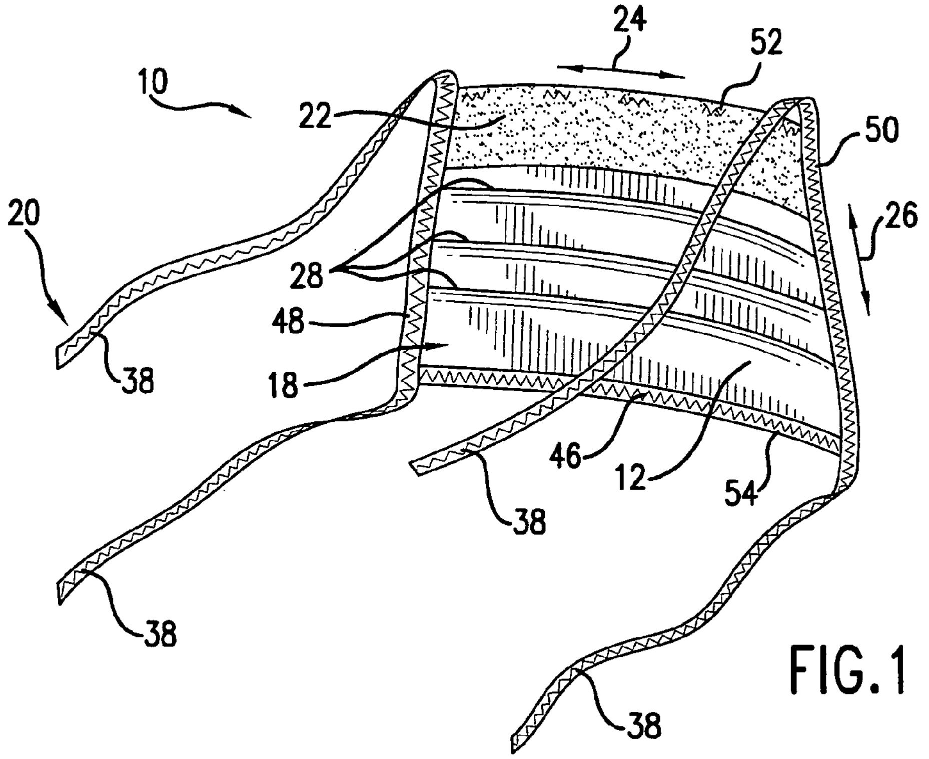
FIG. 1 is a perspective view of a face mask in accordance with one exemplary embodiment that has an absorbent element located on the inner surface.

FIG. 1 is a perspective view of the face mask 10 in accordance with one exemplary embodiment. The face mask 10 includes a body portion 12 that has an inner surface 18 that is configured for facing and contacting the face of a user 14 (FIG. 2) when the face mask 10 is worn. The absorbent element 22 is shown as a horizontal strip of material that is attached to the upper edge of the inner surface 18. The absorbent element 22 is attached to the inner surface 18 of the body portion 12 in any manner as is commonly known to one having ordinary skill in the art. For instance, the absorbent element 22 may be attached to the inner surface 18 through ultrasonic bonding, adhesion, and/or through mechanical fasteners such as staples in accordance with various exemplary embodiments. As such, the absorbent element 22 may be a separate external component attached to the body portion 12. Additionally, it is to be understood that the absorbent element 22 need not be a separate element that is attached to the inner surface 18 of the body portion 12 in accordance with other exemplary embodiments. For example, the absorbent element 22 may be an area of the body portion 12 that is treated or otherwise manufactured so as to have the desired absorbent properties.

Figure 2:
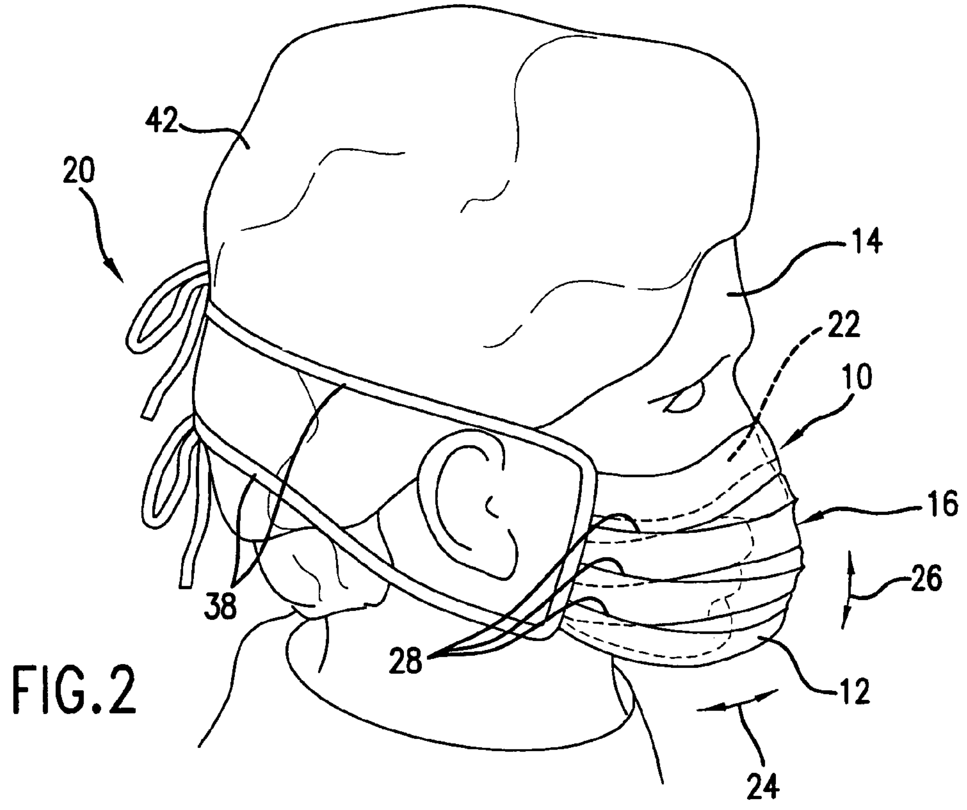
FIG. 2 is a perspective view of the face mask of FIG. 1 shown attached to a user.

FIG. 2 is a perspective view of the face mask 10 of FIG. 1 shown attached to the face of the user 14. The absorbent element 22 acts to absorb moisture and/or condensation from respiration or perspiration of the user 14. Aside from reducing or eliminating fogging on eye wear that may be worn by the user 14, the absorbent element 22 may also act to reduce and/or eliminate condensation that may accumulate on the face of the user 14 and potentially result in irritation of the user 14.

Figure 3:
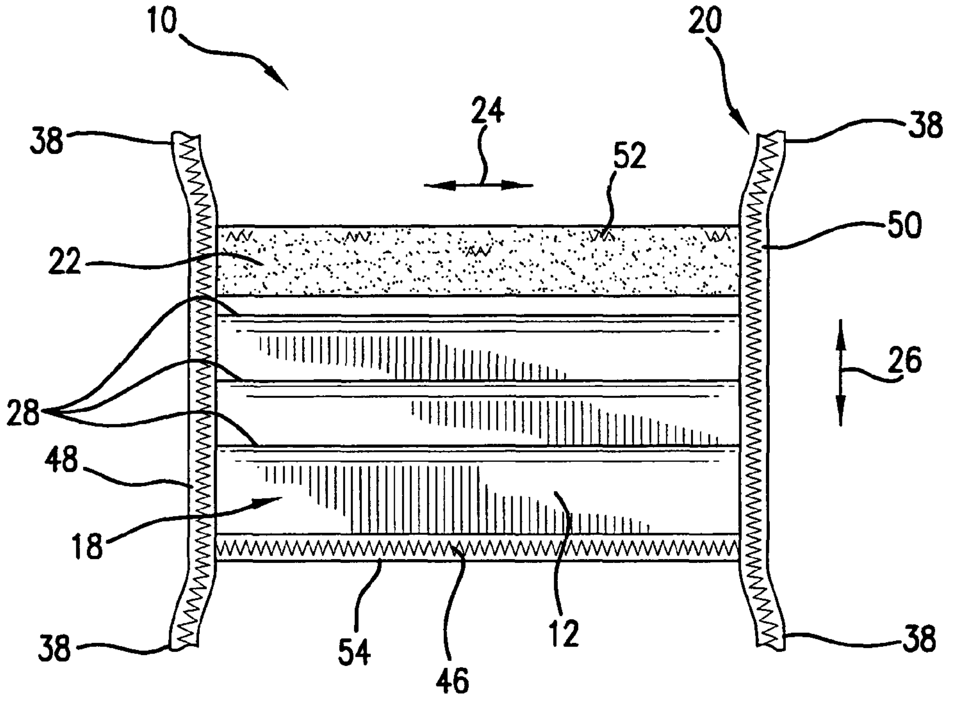
FIG. 3 is a back view of the face mask of FIG. 1.

FIG. 3 shows the inner surface 18 of the body portion 12 of an exemplary embodiment of the face mask 10. The absorbent element 22 is a strip of material that is located across the entire horizontal length 24 of the body portion 12. When placed onto the user 14 (FIG. 2) the absorbent element 22 contacts the nose and cheeks of the user 14 and absorbs moisture and/or condensation in this location. The body portion 12 is provided with a plurality of folds 28 that extend across the horizontal length 24. The folds 28 may be opened by the user 14 so as to adjust the size of the body portion 12 in the vertical length 26. The folds 28 allow for adjustment of the body portion 12 so as to allow for a better fit on the face of the user 14 and formation of a breathing chamber. The body portion 12 may form a breathing chamber with the perimeter of the chamber sealing to the face of the user 14 in certain exemplary embodiment. Although shown as extending across the entire horizontal length 24, the folds 28 may extend only part way across the body portion 12 in accordance with various exemplary embodiments. Additionally, the folds 28 may be provided in any number and may be oriented at any angle on the body portion 12. For instance, the folds 28 may run at a 45° angle to the horizontal length 24. Alternatively or additionally, the folds 28 may run along the vertical length 26 of the body portion 12. It is to be understood, however, that folds 28 are not present in accordance with other exemplary embodiments.

Bindings 48 and 50 may act to limit the vertical extension of the edges of the body portion 12 when the folds 28 are unfolded. As such, bindings 48 and 50 may be present in order to help provide for a desired shape of the body portion 12. Additionally, bindings 52 and 54 may also act to limit extension of the edges of the body portion 12 when folds 28 are unfolded. This may also be the case if folds 28 are provided in orientations along both the horizontal and vertical lengths 24 and 26 of the body portion 12. As such, bindings 52 and 54 may also be employed in order to achieve a desired shape of the body portion 12.

The folds 28 in the body portion 12 may be of any type commonly known to those having ordinary skill in the art. The side edges of the layers 32, 34 and 36 may be held together by any method commonly known to one having ordinary skill in the art. For example, staples or adhesion may be used to hold the layers 32, 34 and 36 together. Additionally or alternatively, ultrasonic bonding, as represented by ultrasonic bond dimples 46, may be used in order to hold the layers 32, 34 and 36 together. It is to be understood that other ultrasonic bonding patterns may be employed to facilitate holding of the layers 32, 34 and 36 to one another. FIG. 3 shows bindings 48 and 50 on either side of the body portion 12 used in order to constrain unfolding of the layers 32, 34 and 36. Additionally, binding 52 may be located on the top edge of the body portion 12 and binding 54 may be located on the bottom edge of the body portion 12. The bindings 48, 50, 52 and 54 may be of any type commonly known to one having ordinary skill in the art. Bindings 48, 50, 52 and 54 act to secure the absorbent element 22 to the body portion 12 in accordance with various exemplary embodiments.

The absorbent element 22 may additionally act to seal the periphery of the upper edge of the body portion 12 so that warm, moist exhaled breath cannot be directed therethrough. The absorbent element 22 may be configured structurally as that shown in U.S. Pat. No. 6,520,181 to Baumann, et al., the entire contents of which are incorporated herein by reference in their entirety for all purposes. The absorbent element 22 need not be configured as a seal in other exemplary embodiments.

Figure 4:
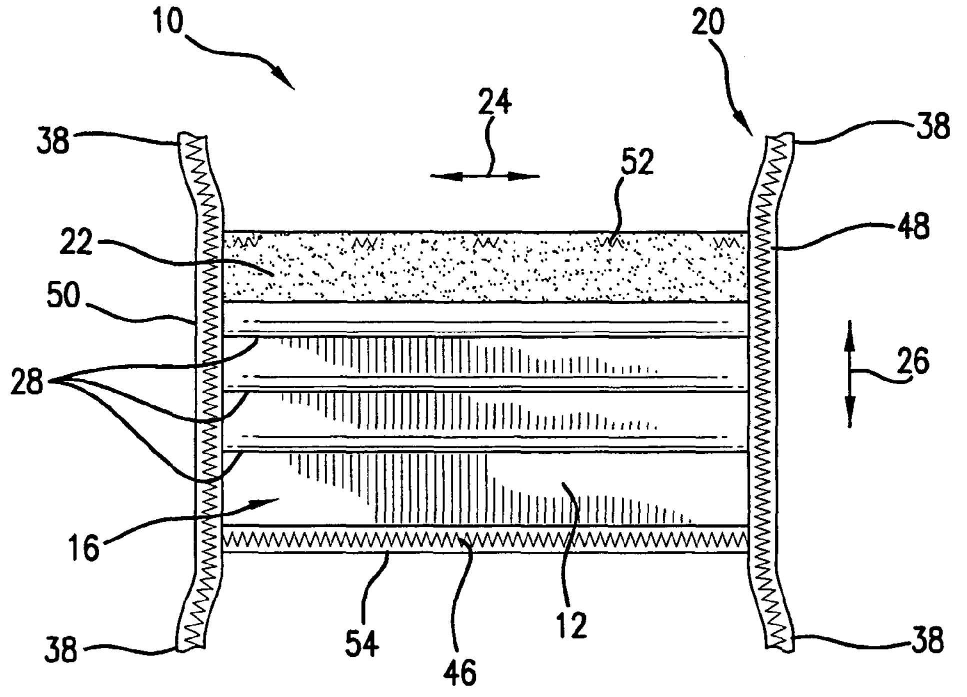
FIG. 4 is a front view of a face mask in accordance with one exemplary embodiment. The absorbent element is shown as a horizontal strip and is located on the outer surface of the body portion of the face mask.

A front view that shows the outer surface 16 of the body portion 12 of face mask 10 in accordance with another exemplary embodiment is shown in FIG. 4. Here, the absorbent element 22 is a separate piece of material that is located on the top edge of the body portion 12 and attached to the outer surface 16 instead of the inner surface 18 as shown in FIGS. 1-3. Placement on the outer surface 16 may be more effective as the absorbent element 22 may actually contact a face shield worn by the user 14 (FIG. 2) and draw moisture and condensation therefrom. Additionally, placement on the outer surface 16 may also be advantageous in the fact that the absorbent element 22 may be closer to the eye wear worn by the user 14 and may not have material of the body portion 12 located between the absorbent element 22 and the eye wear worn by the user 14. This type of an arrangement may be advantageous in that moisture and/or condensation may be more easily absorbed by the absorbent element 22. However, it is to be understood that in accordance with other exemplary embodiments that placement of the absorbent element 22 on the inner surface 18 is more advantageous in that the absorbent element 22 may or may not be closer to the eye wear worn by the user 14 and it is desirable to have additional material between the absorbent element 22 and the eye wear worn by the user 14.

Figure 5:
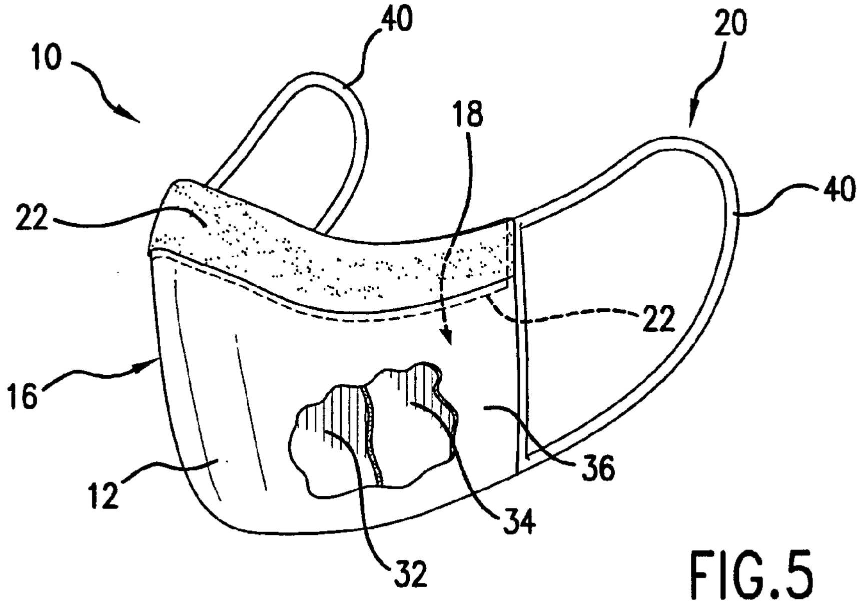
FIG. 5 is a perspective view of an exemplary embodiment of a face mask.

FIG. 5 shows an alternative exemplary embodiment of the face mask 10 in which the absorbent element 22 is located on both the outer surface 16 and the inner surface 18 of the body portion 12. The absorbent element 22 is shown located on the upper edge of the body portion 12. It is to be understood, however, that in accordance with other exemplary embodiments that the absorbent element 22 is located at any location on the outer surface 16 and/or the inner surface 18. For instance, the absorbent element 22 may be located on the entire outer surface 16 and/or on the entire inner surface 18. Additionally, the absorbent element 22 may be located on the bottom edge of the body portion 12 as opposed to the top edge of the body portion 12 as shown in FIGS. 1-5. Additionally, the absorbent element 22 may be variously shaped in accordance with other exemplary embodiments. In this regard, the absorbent element 22 may be disc shaped, star shaped, triangular shaped and/or square shaped in accordance with various exemplary embodiments. Various exemplary embodiments are therefore included in which the absorbent element 22 is located at one or more locations on the outer surface 16 and/or the inner surface 18 and configured in any shape or pattern as is commonly known to one having ordinary skill in the art.

The body portion 12 is shown as being made of a plurality of layers 32, 34 and 36. Layer 32 may be an inner layer of the body portion 12 and have the inner surface 18 defined thereon. Layer 36 may be an outer layer of the body portion 12 and have the outer surface 16 defined thereon. Further, layer 34 may be an intermediate layer located between the layers 32 and 36. It is to be understood, however, that the body portion 12 may be made of any number of layers in accordance with various exemplary embodiments. For instance, the body portion 12 can be made of a single layer in accordance with one exemplary embodiment. Alternatively, the body portion 12 can be made of three layers, five layers, seven layers, ten or fifteen layers in accordance with various exemplary embodiments.

FIG. 6 shows an exemplary embodiment of the face mask 10 in which the absorbent element 22 is located on the inner surface 18 of the body portion 12. The absorbent element 22 is configured on the inner surface 18 so as to surround an area 30 of the inner surface 18. The area 30 is the portion of the inner surface 18 proximate to the mouth or nostrils of the user 14 (FIG. 2). As such, the absorbent element 22 surrounds the mouth and nostrils of the user 14 and absorbs moisture and/or condensation therefrom in order to prevent fogging of eye wear worn by the user 14.

FIG. 7 is an exemplary embodiment of the face mask 10 in which the absorbent element 22 surrounds the entire perimeter of the body portion 12. Although shown as being located on the inner surface 18, it is to be understood that the absorbent element 22 may surround the perimeter of the outer surface 16 in accordance with other exemplary embodiments. Additionally, the face mask 10 may be configured so as to have the absorbent element 22 located around the perimeter of the body portion 12 on both the outer surface 16 and inner surface 18 of the body portion 12. Additionally, other exemplary embodiments exist in which the absorbent element 22 surrounds most of, but not all of, the perimeter of the body portion 12.

Aside from absorbing moisture and/or condensation, the absorbent element 22, as shown for instance in FIGS. 1 and 2, may also be configured so as to be a seal in order to prevent moisture and/or condensation from traveling from the inside of the face mask 10 to the eye wear worn by the user 14. The absorbent element 22 may be configured so as to seal one or more edges of the body portion 12. Additionally, the exemplary embodiments shown in FIGS. 6 and 7 may be configured so that the absorbent element 22 is a seal. As such, in FIG. 6 the absorbent element 22 may act to prevent moisture and/or condensation from escaping the area 30 while in the exemplary embodiment of FIG. 7 the absorbent element 22 may act to prevent moisture and/or condensation from traveling past the perimeter of the inner surface 18 of the body portion 12.

The absorbent element 22 may be configured as a seal as that disclosed in U.S. Pat. No. 6,062,220 to Whitaker, et al., the entire contents of which are incorporated herein by reference in their entirety for all purposes. Additionally or alternatively, the absorbent element 22 may be configured so as to be only a partial seal. In this regard, the absorbent element 22 may act as a seal to prevent some of, but not all of, the moisture and/or condensation from traveling between the absorbent element 22 and the face of the user 14. It is to be understood, however, that in accordance with other exemplary embodiments that the absorbent element 22 is not configured as a seal. In this regard, the absorbent element 22 contacts the face of the user 14 but does not form a seal therewith. It is to be understood that various exemplary embodiments exist in which the absorbent element 22 may or may not prevent fogging through sealing action.

The absorbent element 22 may be added to any type of face mask 10. The absorbent element 22 may reduce fogging by absorbing moisture and/or condensation by exhaled air or perspiration of the user 14 (FIG. 2) and may or may not reduce fogging by acting as a sealing element. The absorbent element 22 may be made of a material that is naturally absorbent. For example, the absorbent element 22 may be made of a material that includes cellulosic fibers. In accordance with one exemplary embodiment, the absorbent element 22 is a wet laid material. Further exemplary embodiments exist in which the absorbent element 22 is a urethane foam, a cellulosic sponge, a urethane film, and/or a urethane non-woven material. In accordance with other exemplary embodiments, the absorbent element 22 is made of any number of materials and is not limited to being made of a single material.

In accordance with one exemplary embodiment, the absorbent element 22 is made of a HYDROKNIT® material as manufactured by Kimberly-Clark Worldwide, Inc. having offices located at 401 North Lake Street, Neenah, Wis., 54957. A hydroknit material is a hydrophilic material manufactured using jets of water in order to bond soft absorbent paper fibers to strong polypropylene non-woven fabric.

Other exemplary embodiments exist in which the absorbent element 22 may be made of a hydrophobic material, such as polypropylene, and treated so as to achieve a desired absorbency. Alternatively, the absorbent element 22 may be a hydrophobic foam that is treated so as to be hydrophilic in order to achieve a desired absorbency. As such, exemplary embodiments exist in which the absorbent element 22 is initially a hydrophilic material, or a hydrophobic material that is treated so as to be capable of achieving a desired degree of absorbency.

In accordance with another exemplary embodiment, the absorbent element 22 is a material that is treated with a surfactant to as to increase the hydrophilic property of the absorbent element 22 so that the absorbent element 22 is more liquid absorbent. As such, various exemplary embodiments exist in which the absorbent element 22 is any type or types of materials that are treated with surfactant based chemistry so as to have increase absorbency.

The absorbent element 22 is a single type of material in accordance with various exemplary embodiments. Alternatively, the absorbent element 22 is made of multiple types of materials in other exemplary embodiments. For instance, the absorbent element 22 may be a laminate made of two or more layers of different materials in accordance with various exemplary embodiments. In accordance with one exemplary embodiment, the absorbent element 22 is a laminate that is formed from a film and a polyurethane foam. The laminate ay be treated with a surfactant such as Gemtex 33 manufactured by FINETEX®, Inc. located at 418 Falmouth Avenue, P.O. Box 216, Elmwood Park, N.J. 07407. In accordance with one exemplary embodiment, the film layer of the laminate making up the absorbent element 22 is attached to the inner surface 18 and the polyurethane foam layer is located on top of the film and in contact with the face of the user 14 when worn.

Another exemplary embodiment exists in which the absorbent element 22 is a spunbound, meltblown material. The spunbound, meltblown material is treated with a surfactant such as MASIL®, manufactured by BASF® Corporation located at 3000 Continental Drive North, Mount Olive, N.J. 07828, so as to have an increased absorbency. Additionally or alternatively, a surfactant such as E-230 FQ Bermocoll manufactured by Akzo Nobel Cellulosic Specialties located at 99 Hewley Lane, Stratford, Conn. 06614, may be used so as to enhance the absorbency of the material making up the absorbent element 22. As such, various exemplary embodiments are included in which the absorbent element 22 is made of one or more types of materials and one or more surfactants. Alternatively, exemplary embodiments exist in which the absorbent element 22 is made of only one or more materials without one or more surfactants present.

Another exemplary embodiment exists in which the absorbent element 22 is a spunbond film laminate that is treated with a surfactant such as DOSS70D which is manufactured by manufacturers Chemicals, L.P., located at 4325 Old Tasso Road, P.O. Box 2788, Cleveland, Tenn. 37312.

The absorbent element 22 may be made of a material as is commonly known to one have ordinary skill in the art. The absorbent element 22 may be made of a material or materials such as those disclosed in U.S. Pat. No. 6,520,181 to Baumann, et al., the entire contents of which are incorporated herein by reference in their entirety for all purposes. However, it is to be understood that the absorbent element 22 used may be selected or treated so as to be capable of absorbing at least 3.5 grams of water.

It is to be understood, however, that the body portion 12 can be of a variety of styles and geometries, such as, but not limited to, flat half masks, pleated face masks, cone masks, duckbill style masks, trapezoidally shaped masks, etc. The styles shown in the Figures are for illustrative purposes only. The body portion 12 may be configured as that shown in U.S. Pat. No. 6,484,722 to Bostock, et al., the entire contents of which are incorporated by reference herein in their entirety for all purposes. As shown in FIG. 2, the face mask 10 may isolate the mouth and the nose of the user 14 from the environment. The face mask 10 may be attached to the user 14 by a fastening member 20 that may be a pair of manual tie straps 38 that are wrapped around the head of the user 14 (and a hair cap 42 if worn by the user 14) and are connected to one another. It is to be understood, however, that other types of fastening members 20 are employed in accordance with various exemplary embodiments. For instance, instead of the manual tie straps 38, the face mask 10 may be attached to the user 14 by a fastening member 20 that may be ear loops 40 (FIG. 5), elastic bands wrapped around the head of the user 14, a hook and loop type fastener arrangement, or a connection directly attaching the face mask 10 to the hair cap 42.

Additionally, the configuration of the face mask 10 is different in accordance with various exemplary embodiments. In this regard, the face mask 10 can be made in order to cover both the eyes, hair, nose, throat, and mouth of the user 14. As such, the present invention includes face masks 10 that cover areas above and beyond simply the nose and mouth of the user 14. The face mask 10 may also incorporate any combination of known face mask 10 features, such as visors or shields, sealing films, beard covers, etc. Exemplary face masks and features incorporated into face masks are described and shown, for example, in the following U.S. Patents: U.S. Pat. Nos. 4,802,473; 4,969,457; 5,322,061; 5,383,450; 5,553,608; 5,020,533; and 5,813,398. The entire contents of these patents are incorporated by reference herein in their entirety for all purposes.

The exemplary embodiment shown in FIG. 7 includes a series of structural elements (stays) 44 incorporated into the body portion 12 in order to provide for a face mask 10 with different desired characteristics. The stays 44 provide for structural rigidity of the body portion 12, and may also be shaped in order to help seal the periphery of the body portion 12. Alternatively, a stay 44 may be employed within the body portion 12 in order to help conform the body portion 12 around the nose of the user 14 (FIG. 2). The stay or stays 52 may be used to help seal the perimeter of the body portion 12 around the face of the user 14 and/or to help maintain the shape of a breathing chamber and to keep the breathing chamber from the face of the user 14.

Additionally, a stay 44 may be employed in order to better shape the body portion 12 around the chin of the user 14 (FIG. 2). The stays 44 may allow for a better fit of the body portion 12 and may be used to help form a chamber around the mouth and/or nose of the user 14. The stays 44 may help achieve a better fit so as to prevent the transfer of pathogens through any possible openings along the perimeter of the body portion 12. A series of stays 44 incorporated into a face mask 10 is disclosed in U.S. Pat. No. 5,699,791, to Sukiennik et al., the entire contents of which are incorporated herein by reference in their entirety for all purposes. Stays 44 may be made of an elongated malleable member such as a metal wire or an aluminum band that can be formed into a rigid shape in order to impart this shape into the body portion 12 of the face mask 10. Of course, various exemplary embodiments exist that do not include stays 44.

The intermediate layer 34, as shown in FIG. 5, may be a filtration media configured to prevent the passage of pathogens through the body portion 12 while still allowing for the passage of air in order to permit the user 14 (FIG. 2) to breath. As can be imagined, the layers 32, 34 and 36 may be configured so that any of the layers 32, 34 and 36 include filtration media. For instance, both of the layers 32 and 36 may include filtration media in accordance with one exemplary embodiment.

The layers 32, 34 and 36 may be constructed from various materials known to those skilled in the art. For instance, the layer 36 of the body portion 12 may be any nonwoven web, such as a spunbonded, meltblown, or coform nonwoven web, a bonded carded web, or a wetlaid composite. The layer 36 of the body portion 12 and layer 32 may be a necked nonwoven web or a reversibly necked nonwoven web. The layers 32, 34 and 36 may be made of the same material or of different materials.

Many polyolefins are available for nonwoven web production, for example polyethylenes such as Dow Chemical's ASPUN® 6811A linear polyethylene, 2553 LLDPE and 25355, and 12350 polyethylene are such suitable polymers. Fiber forming polypropylenes include, for example, Exxon Chemical Company's Escorene® PD 3445 polypropylene and Basell's PF-304. Many other suitable polyolefins are commercially available as are known to those having ordinary skill in the art.

The various materials used in construction of the face mask 10 may include a necked nonwoven web, a reversibly necked nonwoven material, a neck bonded laminate, and elastic materials such as an elastic coform material, an elastic meltblown nonwoven web, a plurality of elastic filaments, an elastic film, or a combination thereof. Such elastic materials have been incorporated into composites, for example, in U.S. Pat. No. 5,681,645 to Strack et al., U.S. Pat. No. 5,493,753 to Levy et al., U.S. Pat. No. 4,100,324 to Anderson et al., and in U.S. Pat. No. 5,540,976 to Shawver et al, the entire contents of these patents are incorporated herein by reference in their entirety for all purposes. In an exemplary embodiment where an elastic film is used on or in the body portion 12, the film may be sufficiently perforated to ensure that the user 14 (FIG. 2) can breathe through the body portion 12 if the face mask 10 is desired to be breathable in this location.

The intermediate layer 34 when configured as a filtration layer may be a meltblown nonwoven web and, in some embodiments, is electret treated. Electret treatment results in a charge being applied to the intermediate layer 34 that further increases filtration efficiency by drawing particles to be filtered toward the intermediate layer 34 by virtue of their electrical charge. Electret treatment can be carried out by a number of different techniques. One technique is described in U.S. Pat. No. 5,401,446 to Tsai et al., the entire contents of which are incorporated herein by reference in their entirety for all purposes. Other methods of electret treatment are known in the art, such as that described in U.S. Pat. No. 4,215,682 to Kubik et al.; U.S. Pat. No. 4,375,718 to Wadsworth; U.S. Pat. No. 4,592,815 to Nakao; and U.S. Pat. No. 4,874,659 to Ando, the entire contents of these patents are incorporated herein by reference in their entirety for all purposes.

The intermediate layer 34 may be made of an expanded polytetrafluoroethylene (PTFE) membrane, such as those manufactured by W. L. Gore & Associates. A more complete description of the construction and operation of such materials can be found in U.S. Pat. Nos. 3,953,566 and 4,187,390 to Gore, the entire contents of these patents are incorporated herein by reference in their entirety for all purposes. The expanded polytetrafluoroethylene membrane may be incorporated into a multi-layer composite, including, but not limited to, an outer nonwoven web layer 36, an extensible and retractable layer, and an inner layer 32 comprising a nonwoven web.

SMS may be used to comprise the layers 32, 34 and 36. SMS is a material that is made of meltblown fibers between two spunbond layers made of spunbonded fibers.

Multiple layers of the face mask 10 may be joined by various methods, including adhesive bonding, thermal point bonding, or ultrasonic bonding. Although shown as having three layers 32, 34 and 36, it is to be understood that in other exemplary embodiments of the present invention, that the body portion 12 and/or the entire face mask 10 may be made of any number of layers.

The body portion 12 of the face mask 10 may be made of inelastic materials. Alternatively, the material used to construct the body portion 12 may be comprised of elastic materials, allowing for the body portion 12 to be stretched over the nose, mouth, and/or face of the user 14. (FIG. 2) The face mask 10 of the present invention may be made of an elastic material that allows the face mask 10 to stretch in one or more directions. The use of an elastic material incorporated into the body portion 12 may allow for fuller coverage of the user's 14 face and provide for more flexibility in accommodating variously sized faces of the users 14. Alternatively, the body portion 12 may be made of an inelastic material. As such, the material that makes up the face mask 10 may exhibit elastic or inelastic characteristics depending upon the user's 14 needs.

The body portion 12 of the face mask 10 may be configured so that it is capable of stretching across the face of the user 14 (FIG. 2) from ear to ear and/or nose to chin. The ability of the body portion 12 to stretch and recover may provide the face mask 10 with better sealing capabilities and a more comfortable fit than face masks 10 that have an inelastic body portion 12. In order for the body portion 12 to stretch and recover, the body portion 12 may have at least one layer or a material that has stretch and recovery properties. Additionally, the entire face mask 10 may be composed of a material that has stretch and recovery properties in other exemplary embodiments. In certain exemplary embodiments, the percent recovery is about 15% and the percent stretch is between about 15-65%, in other embodiments the percent recovery is between about 20-40% stretch, and in still other embodiments the percent recovery is between about 25-30% stretch.

Elastomeric thermoplastic polymers may be used in the face mask 10 and may include block copolymers having the general formula A-B-A' or A-B, where A and A' are each a thermoplastic polymer endblock which contains a styrenic moiety such as a poly (vinyl arene) and where B is an elastomeric polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. Examples of useful elastomeric resins include those made from block copolymers such as polyurethanes, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene) and the like.

One or more layers 32, 34 and 36 of the face mask 10 may be made of a composite that is a neck bonded laminate in certain exemplary embodiments. The neck bonded laminate may utilize a necked material or a reversibly necked material. The necking process typically involves unwinding a material from a supply roll and passing it through a brake nip roll assembly at a given linear speed. A take-up roll or nip, operating at a linear speed greater than that of the brake nip roll, draws the material and generates the tension needed to elongate and neck the fabric. When a reversibly necked material is desired, the stretched material is heated and cooled while in a stretched condition. The heating and cooling of the stretched material causes additional crystallization of the polymer and imparts a heat set. The necked material or reversibly necked material is then bonded to an elastic material. Afterwards, the layer may be folded in order to form folds 28. The resulting necked composite is extensible and retractable in the cross-machine direction, that is the direction perpendicular to the direction the material is moving when it is produced. Upon extension and release, the elastic material provides the force needed for the extended composite to retract.

In another exemplary embodiment, the composite making up one or more of the layers 32, 34 and 36 may be a stretch bonded laminate. A stretch bonded laminate is formed by providing an elastic material, such as a nonwoven web, filaments, or film, extending the elastic material, attaching it to a gatherable material, and releasing the resulting laminate. A stretch bonded laminate is extensible and retractable in the machine direction, that is the direction that the material is moving when it is produced. A composite with multiple layers may be formed by providing the elastic layer and the gatherable layers, and subjecting it to this process either simultaneously or stepwise. The stretch bonded laminate may also include a necked material that is extensible and retractable in the cross-direction such that the overall laminate is extensible and retractable in at least two dimensions. As an illustration, to construct a two-layer composite that is extensible and retractable in at least two dimensions, an elastomeric meltblown nonwoven web is provided, the elastomeric meltblown nonwoven web is then extended in the machine direction, and the necked spunbonded nonwoven material is attached to the elastomeric meltblown nonwoven web by thermal bonding while the elastomeric meltblown web is extended. When the biasing force is released, the resulting composite is extensible and retractable in both the cross-direction and machine direction, due to the extensibility of the necked material and the use of the stretch bonding process, respectively. The composite may then be folded in order to form folds 28 and attached to or otherwise incorporated with one or more layers to make up the body portion 12.

Additional examples of processes to make such composites are described in, but not limited to, U.S. Pat. No. 5,681,645 to Strack et al., U.S. Pat. No. 5,492,753 to Levy et al., U.S. Pat. No. 4,100,324 to Anderson et al., and in U.S. Pat. No. 5,540,976 to Shawver et al., the entire contents of these patents are incorporated herein by reference in their entirety for all purposes.

The composite may contain various chemical additives or topical chemical treatments in or on one or more layers, including, but not limited to, surfactants, colorants, antistatic chemicals, antifogging chemicals, fluorochemical blood or alcohol repellents, lubricants, or antimicrobial treatments.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

Sample Tests Carried Out In Accordance With Various Exemplary Embodiments

A face mask 10 that included an absorbent element 22 in the form of an absorbent foam was attached to a breathing mannequin head. The breathing mannequin head exhaled warm, moist air in order to simulate human respiration. Eye wear was placed on the mannequin and the performance of the face mask was evaluated. The absorbent element 22 was found to successfully absorb moisture exhaled by the mannequin. The absorbent element 22 was an absorbent foam material.

A face mask 10 was also provided with an absorbent element 22 that was an absorbent laminate. The face mask 10 was applied to the head of a mannequin capable of exhaling warm, moist air in order to simulate human respiration. Eye wear were placed on the mannequin and the performance of the face mask 10 was evaluated. The absorbent laminate making up the absorbent element 22 was found to successfully redirect airflow away from the eye wear resulting in fewer incidences of fogging, and the absorbent element 22 was found to successfully absorb moisture from the exhaled air of the mannequin.

What is claimed:

1. A face mask, comprising:

a body portion configured to be placed over a mouth and at least part of a nose of a user in order to isolate the mouth and the at least part of the nose of the user from the environment such that respiration air is drawn through said body portion and subsequently exhaled by the user through said body portion, wherein said body portion has an outer exposed surface facing away from the user when worn, wherein said body portion has an inner exposed surface facing towards the user and wherein said inner surface is configured to contact the face of the user when worn;

a fastening member attached to said body portion and configured for retaining said body portion onto the face of a user; and an absorbent element located on at least one of said exposed inner and exposed outer surfaces of said body portion so that the absorbent element has a first side adjacent to one of said exposed inner and exposed outer surfaces and a second side opposite to the first side that is completely exposed to either the user or the environment, wherein said absorbent element is configured for retaining liquid, and wherein said absorbent element is capable of absorbing at least 3.5 grams of water, wherein said absorbent element is located on said outer surface of said body portion.

2. A face mask, comprising:

a body portion configured to be placed over a mouth and at least part of a nose of a user in order to isolate the mouth and the at least part of the nose of the user from the environment such that respiration air is drawn through said body portion and subsequently exhaled by the user through said body portion, wherein said body portion has an outer exposed surface facing away from the user when worn, wherein said body portion has an inner exposed surface facing towards the user and wherein said inner surface is configured to contact the face of the user when worn;

a fastening member attached to said body portion and configured for retaining said body portion onto the face of a user; and an absorbent element located on at least one of said exposed inner and exposed outer surfaces of said body portion so that the absorbent element has a first side adjacent to one of said exposed inner and exposed outer surfaces and a second side opposite to the first side that is completely exposed to either the user or the environment, wherein said absorbent element is configured for retaining liquid, and wherein said absorbent element is capable of absorbing at least 3.5 grams of water, wherein said absorbent element is located on both said outer surface and said inner surface of said body portion.

3. A face mask, comprising:

a body portion configured to be placed over a mouth and at least part of a nose of a user in order to isolate the mouth and the at least part of the nose of the user from the environment such that respiration air is drawn through said body portion and subsequently exhaled by the user through said body portion, wherein said body portion has an outer exposed surface facing away from the user when worn, wherein said body portion has an inner exposed surface facing towards the user and wherein said inner surface is configured to contact the face of the user when worn;

a fastening member attached to said body portion and configured for retaining said body portion onto the face of a user; and an absorbent element located on at least one of said exposed inner and exposed outer surfaces of said body portion so that the absorbent element has a first side adjacent to one of said exposed inner and exposed outer surfaces and a second side opposite to the first side that is completely exposed to either the user or the environment, wherein said absorbent element is configured for retaining liquid, and wherein said absorbent element is capable of absorbing at least 3.5 grams of water, wherein said absorbent element is located on one of said surfaces of said body portion so as to form a perimeter bounding an area of said surface.

4. A face mask, comprising:

a body portion configured to be placed over a mouth and at least part of a nose of a user in order to isolate the mouth and the at least part of the nose of the user from the environment such that respiration air is drawn through said body portion and subsequently exhaled by the user through said body portion, wherein said body portion has an outer exposed surface facing away from the user when worn, wherein said body portion has an inner exposed surface facing towards the user and wherein said inner surface is configured to contact the face of the user when worn;

a fastening member attached to said body portion and configured for retaining said body portion onto the face of a user; and an absorbent element located on at least one of said exposed inner and exposed outer surfaces of said body portion so that the absorbent element has a first side adjacent to one of said exposed inner and exposed outer surfaces and a second side opposite to the first side that is completely exposed to either the user or the environment, wherein said absorbent element is configured for retaining liquid, and wherein said absorbent element is capable of absorbing at least 3.5 grams of water, wherein said absorbent element is located around the perimeter of said surface.

5. A face mask, comprising:

a body portion configured to be placed over a mouth and at least part of a nose of a user that has an outer exposed surface when worn on the face of a user and an inner surface oppositely disposed to said outer surface and wherein said inner surface is exposed to the face of the user and configured to contact the face when worn: and an absorbent element located on at least one of said exposed inner and exposed outer surfaces of said body portion so that the absorbent element has a first side adjacent to one of said exposed inner and exposed outer surfaces and a second side opposite to the first side that is completely exposed to either the user or the environment, wherein said absorbent element is capable of absorbing at least 3.5 grams of water, wherein said absorbent element is located on said outer surface of said body portion.

6. A face mask, comprising:

a body portion configured to be placed over a mouth and at least part of a nose of a user that has an outer exposed surface when worn on the face of a user and an inner surface oppositely disposed to said outer surface and wherein said inner surface is exposed to the face of the user and configured to contact the face when worn; and an absorbent element located on at least one of said exposed inner and exposed outer surfaces of said body portion so that the absorbent element has a first side adjacent to one of said exposed inner and exposed outer surfaces and a second side opposite to the first side that is completely exposed to either the user or the environment, wherein said absorbent element is capable of absorbing at least 3.5 grams of water, wherein said absorbent element is located on one of said inner or outer exposed surfaces of said body portion so as to form a perimeter bounding an area of said surface.

7. A face mask, comprising:

a body portion configured to be placed over a mouth and at least part of a nose of a user that has an outer exposed surface when worn on the face of a user and an inner surface oppositely disposed to said outer surface and wherein said inner surface is exposed to the face of the user and configured to contact the face when worn; and an absorbent element located on at least one of said exposed inner and exposed outer surfaces of said body portion so that the absorbent element has a first side adjacent to one of said exposed inner and exposed outer surfaces and a second side opposite to the first side that is completely exposed to either the user or the environment, wherein said absorbent element is capable of absorbing at least 3.5 grams of water, wherein said absorbent element is located around the perimeter of said inner exposed surface.

8. A face mask, comprising:

a body portion that has an exposed outer surface when worn on the face of a user and an inner surface oppositely disposed to said outer surface, said inner surface being exposed to the face of the user and configured to contact the face when worn on the face; and an absorbent element located on at least one of said exposed inner and exposed outer surfaces of said body portion so that the absorbent element has a first side adjacent to one of said exposed inner and exposed outer surfaces and a second side opposite to the first side that is completely exposed to either the user or the environment, wherein said absorbent element is treated with a surfactant so as to increase the hydrophilic property of said absorbent element such that said absorbent element is more liquid absorbent, wherein said absorbent element is located on one of said inner or outer exposed surfaces of said body portion so as to form a perimeter bounding an area of said surface.

9. A face mask, comprising:

a body portion that has an exposed outer surface when worn on the face of a user and an inner surface oppositely disposed to said outer surface, said inner surface being exposed to the face of the user and configured to contact the face when worn on the face; and an absorbent element located on at least one of said exposed inner and exposed outer surfaces of said body portion so that the absorbent element has a first side adjacent to one of said exposed inner and exposed outer surfaces and a second side opposite to the first side that is completely exposed to either the user or the environment, wherein said absorbent element is treated with a surfactant so as to increase the hydrophilic property of said absorbent element such that said absorbent element is more liquid absorbent, wherein said absorbent element is located around the perimeter of said inner exposed surface.

* * * * *